US006652882B1

(12) United States Patent
Odidi et al.

(10) Patent No.: US 6,652,882 B1
(45) Date of Patent: Nov. 25, 2003

(54) CONTROLLED RELEASE FORMULATION CONTAINING BUPROPION

(75) Inventors: Isa Odidi, Mississauga (CA); Amina Odidi, Mississauga (CA)

(73) Assignee: Intellipharmaceutics Corp, Mississauga (CA)

( * ) Notice: Subject to any disclaimer, the term of this patent is extended or adjusted under 35 U.S.C. 154(b) by 0 days.

(21) Appl. No.: 09/166,365

(22) Filed: Oct. 5, 1998

Related U.S. Application Data

(60) Provisional application No. 60/061,121, filed on Oct. 6, 1997.

(51) Int. Cl.[7] .......................... A61K 9/10; A61K 9/22; A61K 9/16; A61K 47/38
(52) U.S. Cl. .................. 424/486; 424/487; 424/468; 424/499; 424/501
(58) Field of Search ......................... 424/486, 427, 424/488, 499, 501, 468; 514/772.6, 781, 960, 964

(56) References Cited

U.S. PATENT DOCUMENTS 3,819,706 A * 6/1974 Mehta
4,666,705 A * 5/1987 DeCrosta et al.
5,240,712 A * 8/1993 Smith et al.
5,731,000 A * 3/1998 Ruff et al.

FOREIGN PATENT DOCUMENTS

GB        2 134 516        8/1984

OTHER PUBLICATIONS

Walters, S. M., "Influence of pH on Hydrolytic Decomposition of Dimethylpropion Hydrochloride: Stability Studies on Drug Substance and Tablets Using High–Performance Liquid Chromatography", *J. Pharm. Science,* 69(10): 1208 (1980).

Laizure, S.C. and DeVane, C. L.,, "Stability of Bupropion and Its Major Metabolites in Human Plasma", *Therapeutic Drug Monitoring,* 7(4): 447 (1985).

* cited by examiner

*Primary Examiner*—Edward J. Webman
(74) *Attorney, Agent, or Firm*—Foley Hoag LLP

(57) ABSTRACT

The present invention relates to a controlled release pharmaceutical formulation comprising an effective amount of an active ingredient and from about 1% to about 70% by weight of an uncrosslinked polymer, a crosslinked insoluble polymer or a mixture of uncrosslinked and crosslinked polymers.

65 Claims, No Drawings

CONTROLLED RELEASE FORMULATION CONTAINING BUPROPION

This is a provisional application No. 60/061,121, filed Oct. 6, 1997.

FIELD OF THE INVENTION

The present invention relates to a controlled release formulation for administration of antidepressant drugs such as bupropion to a subject and to antidepressant formulations of improved stability.

BACKGROUND OF THE INVENTION

Bupropion, or (±)-2-(tert-butylamino)3'-chloropropiophenone, is an aminoketone antidepressant. It may be administered in the form of a pharmaceutically acceptable salt, such as bupropion hydrochloride.

Bupropion is extensively metabolised in mammals and on oral administration, only a small portion of the administered dose reaches the systemic circulation intact. For example, the absolute bioavailability of bupropion in mammals such as rats and dogs ranges from 5% to 20%.

It would therefore be useful to employ a controlled release formulation of bupropion.

The stability of bupropion on storage has also been a cause for concern, the compound being subject to hydrolytic decomposition during storage (*Ther. Drug Monit.* (1985), v. 7(y), pp. 447–458; GA (1985), v. 101, pp. 210748e of UX; and *J. Pharm. Sci.* (1980), v. 69, pp. 1206–1209).

Similar problems of active metabolism and storage instability are encountered with many antidepressant drugs.

SUMMARY OF THE INVENTION

It is an object of the present invention to ode a controlled release pharmaceutical formulation containing as active ingredient an antidepressant such as bupropion or a pharmaceutically acceptable bupropion salt, whereby the active ingredient is released over a period of time to provide improved availability of the drug.

It is a further object of the invention to provide controlled release pharmaceutical formulations whereby the active ingredient is released in either a continuous or a pulsatile manner.

In accordance with one embodiment, the invention provides a controlled release pharmaceutical formulation which comprises an effective amount of bupropion hydrochloride and from about 1% to about 70% by weight of a polymer selected from the group consisting of a) at least one uncrosslinked polymer selected from the group consisting of hydroxyethyl cellulose, sodium carboxymethyl cellulose, hydroxypropyl cellulose and hydroxypropylmethyl cellulose; b) at least one crosslinked insoluble polymer; and c) a mixture of (a) and (b).

The formulations of the invention may further comprise a stabilising agent, such as a saturated polyglycolised glyceride. The polyglycolised glyceride may consist of mono-, di- and triglycerides and of mono- and di- fatty acid esters of polyethylene glycol.

DETAILED DESCRIPTION OF THE INVENTION

In accordance with one embodiment, the invention provides controlled release pharmaceutical formulations containing as active ingredient a monocyclic, bicyclic, tricyclic or heterocyclic antidepressant.

In a preferred embodiment, the active ingredient is bupropion or a pharmaceutically acceptable salt of bupropion. Bupropion hydrochloride is especially preferred as active ingredient The controlled release formulations of the invention, in oral dosage form, are prepared by mixing a selected active ingredient with one or more uncrosslinked, linear polymers, or with one or more covalently crosslinked insoluble polymers or with a mixture of uncrosslinked, linear and crosslinked, insoluble polymers.

The present invention is simple in fabrication, permitting efficient and reproducible mass production by conventional techniques.

Suitable polymers for use in the controlled release formulations of the present invention are uncrosslinked, linear polymers including cellulosic polymers, preferably hydroxyethyl cellulose (HEC), sodium carboxymethyl cellulose, hydroxypropylmethyl cellulose and hydroxypropyl cellulose, or covalently crosslinked insoluble polymers such as high molecular weight crosslinked homopolymers and copolymers of acrylic acid (carbopol resins), or mixtures of these uncrosslinked and covalently crosslinked polymers.

In accordance with a further embodiment, the formulations of the invention also include at least one stabilising agent which improves the stability of bupropion hydrochloride on storage of the formulation.

Suitable stabilising agents for use in the formulations of the invention, to reduce the degradation of bupropion hydrochloride on storage, include shellac, any of its constituent aliphatic polyhydroxy acids presented as lactones, lactides and inter-esters, saturated polyglycolised glycerides containing $C_8$ to $C_{18}$ saturated fatty acids such as gelucire, ascorbic acid, benzoic acid and fumaric acid.

Gelucire serves a dual role, providing protective action against oxidation and hydrolysis of bupropion and, also, together with the polymer component, modulating the release of bupropion hydrochloride.

Pharmaceutically acceptable excipients and tablet lubricants may optionally be included in the formulations of the invention. Suitable excipients include sucrose, silicone dioxide, silicified microcrystalline cellulose, fatty acids, fatty acid salts such as metallic salts of stearate, including aluminum-, calcium-, magnesium-, sodium- and zinc stearate, fatty acid esters and talo.

The active ingredient content of the formulations of the invention will depend on the desired dosage and the time frame over which the formulations release the active ingredient For example, if the formulation releases active ingredient over twenty four hours such that one dosage is given daily, ear oral dosage form of the formulation will contain the desired daily dose of active ingredient If two dosages of formulation are to be given daily, each releasing drug over 12 hours, each oral dosage form of the formulation will contain half of a daily drug dose. For example, a controlled release formulation of bupropion hydrochloride should preferably provide 150–400 mg of drug per day.

The formulations of the invention may provide for continuous delivery of active ingredient or for pulsatile delivery. The rate of controlled release of active ingredient, and the pattern of release, for example continuous or pulsatile, is determined by the proportions and type of polymer incorporated into the formulation The polymer content is adjusted to give a desired rate of release, for example over 12 hours, 24 hours or 48 hours. For continuous release, one formulation of a desired rate of release is employed.

Pulsatile delivery is achieved by preparing an oral dosage form, such as a capsule, containing more than one type of tablet or more than one population of granules, each tablet type or granule population releasing the active ingredient at a different rate or at a different time interval; for example, one tablet type or granule population begins drug release first and when the drug level from that release has peaked and begun to decline, a second tablet type or granule population begins drug release, leading to a second peak of drug level. The controlled release formulations of the invention are prepared by mixing bupropion hydrochloride with an uncrosslinked linear polymer, a crosslinked polymer or a mixture of such polymer, wet granulating the mixture with a solution of a stabilising agent and drying the resulting granules, which can be processed into tablets or pellets.

In accordance with a further embodiment, there is provided a method of producing a wax matrix controlled delivery formulation comprising polyglycolised glyceride having the following types of fatty acids: $C_8$ to $C_{18}$ saturated fatty acids, for controlled delivery of bupropion hydrochloride which is stable during storage.

The sustained release characteristics of the formulations of the present invention can be predetermined and varied by adjusting the makeup of the composition as described and exemplified herein. For example, the duration, uniformity and continuity of release of bupropion hydrochloride can be suitably controlled by varying the relative amounts of gelucire and polymer. The finished tablet may be film coated

EXAMPLES

The following specific examples of the controlled release pharmaceutical formulations of the invention are for illustration and are not intended to be limiting in any way.

Example 1

I) Bupropion hydrochloride (1–70% by weight) was blended with 1–60% by weight of a hydroxyethylcellulose polymer (preferably Natrosol® 250HHX PHARM), and optionally lactose or microcrystalline cellulose and/or talc, in a planetary or high shear mixer;

II) The homogenous blend from step I was granulated with a granulating solution of Gelucire 44/14 in isopropyl alcohol in a planetary or high shear mixer. The amount of Gelucire 44/14 is from 1–55% by weight of the dry ingredients. It is preferable to knead the wet mass for 1–3 minutes after wet granulation; III) The wet granules were dried in a fluid bed dryer or tray dryer to a loss on drying (LOD) of <5%. Preferably they may be dried in a tray dryer at >40° C. to an LOD of <2%;

IV) Size reduction of the dried granules from step III was carried out in a Cone mill such that granule size is preferably <1400 microns;

V) The milled granules were intimately blended with a lubricant such as magnesium sterate in a V-blender;

VI) The lubricated granules from step V were compressed into tablets using a rotary tablet press. The resulting tablets had a hardness of >5 Strong Cobb units and friability <1%.

Example 2

Bupropion hydrochloride extended release (ER) tablets: 400 mg

|  | % composition |
| --- | --- |
| Bupropion hydrochloride | 39 |
| Natrosol 250 HHX | 25 |

-continued

Bupropion hydrochloride extended release (ER) tablets: 400 mg

|  | % composition |
| --- | --- |
| Gelucire 44/14 | 30 |
| Talc | 5 |
| Magnesium stearate | 1 |

Bupropion hydrochloride was blended with Natrosol and talc in a high shear mixer until a homogeneous mixture was obtained. This mixture was granulated with gelucire dissolved in isopropyl alcohol and the granules were dried in a fluid bed dryer to a loss on dying of 1.5%. The dried granules were passed through a #14 mesh sieve. The milled granules were blended with magnesium stearate in a V-blender and the treated granules were pressed into tablets using a rotary tablet press.

Example 3

Bupropion hydrochloride ER tablets: 400 mg

|  | % composition |
| --- | --- |
| Bupropion hydrochloride | 39 |
| Na carboxymethyl cellulose | 20 |
| Gelucire 44/14 | 25 |
| Lactose | 10 |
| Talc | 5 |
| Magnesium stearate | 1 |

Bupropion hydrochloride was blended with sodium carboxymethyl cellulose, lactose and talc in a high shear mixer until a homogeneous mixture was obtained. This mixture was granulated with gelucire dissolved in isopropyl alcohol and the granules were dried in a tray dryer to a loss on drying of 1.5%. The dried granules were passed through a #14 mesh sieve. The milled granules were blended with magnesium stearate in a V-blender and the treated granules were pressed into tablets using a rotary tablet press.

Example 4

Bupropion hydrochloride ER tablets: 400 mg

|  | % composition |
| --- | --- |
| Bupropion hydrochloride | 39 |
| Natrosol 250 HHX | 20 |
| Lactose | 10 |
| Gelucire 33/01 | 25 |
| Talc | 5 |
| Magnesium stearate | 1 |

Bupropion hydrochloride was blended with Natrosol 250 HHX, lactose and talc in a high shear mixer until a homogeneous mixture was obtained. This mixture was granulated with gelucire dissolved in isopropyl alcohol and the granules were dried in a tray dryer to a loss on drying of 1.5%. The dried granules were passed through a #14 mesh sieve. The milled granules were blended with magnesium stearate in a V-blender and the treated granules were pressed into tablets using a rotary tablet press.

Example 5

| Bupropion hydrochloride ER tablets: 400 mg | |
|---|---|
| | % composition |
| Bupropion hydrochloride | 39 |
| Carbopol 971 P | 10 |
| Lactose | 20 |
| Gelucire 33/01 | 25 |
| Talc | 5 |
| Magnesium stearate | 1 |

Bupropion hydrochloride was blended with Carbopol, Lactose and talc as described in Example 4 and the remainder of the process was as described in that Example.

Example 6

| Bupropion hydrochloride ER tablets: 400 mg | |
|---|---|
| | % composition |
| Bupropion hydrochloride | 39 |
| Natrosol 250 HHX | 15 |
| Lactose | 10 |
| Carbopol | 5 |
| Talc | 5 |
| Magnesium stearate | 1 |
| Gelucire 33/01 | 25 |

Bupropion hydrochloride was blended with Natrosol, Carbopol, lactose and talc as described in Example 4 and the remainder of the process was as described in that Example.

The present invention is not limited to the features of the embodiments described herein, but includes all variations and modifications within the scope of the claims.

We claim:

1. A controlled release pharmaceutical formulation comprising an effective amount of bupropion hydrochloride and:
   a) from about 20% to about 25% by weight of an uncrosslinked polymer selected from the group consisting of hydroxyethyl cellulose, sodium carboxymethyl cellulose, hydroxypropyl cellulose, hydroxypropylmethyl cellulose, and mixtures thereof; and
   b) from about 1% to about 70% by weight of a crosslinked insoluble polymer.

2. The formulation of claim 1 wherein the crosslinked, insoluble polymer is an acrylic acid polymer.

3. The formulation of claim 2 further comprising a stabilizing agent.

4. The formulation of claim 2 further comprising at least one pharmaceutically acceptable excipient.

5. The formulation of claim 3 wherein the stabilizing agent is selected from the group consisting of shellac and its constituent aliphatic polyhydroxy acids, ascorbic acid, benzoic acid and fumaric acid.

6. The formulation of claim 3 wherein the stabilizing agent comprises a saturated polyglycolised glyceride containing $C_8$ to $C_{18}$ saturated fatty acids.

7. The formulation of claim 6 wherein the saturated polyglycolised glyceride is present in an amount of about 1% to about 75% by weight.

8. The formulation of claim 4 wherein the pharmaceutically acceptable excipient is selected from the group consisting of sucrose, silicone dioxide, silicified microcrystalline cellulose, fatty acids, fatty acid salts, fatty acid esters, talc, and mixtures thereof.

9. The formulation of claim 2 wherein the acrylic acid polymer is a copolymer of acrylic acid.

10. The formulation of claim 6 further comprising a pharmaceutically acceptable film coat.

11. The formulation of claim 6 comprising
   (a) about 20% to about 25% by weight of an uncrosslinked polymer selected from the group consisting of hydroxyethyl cellulose, sodium carboxymethyl cellulose, hydroxypropyl methyl cellulose, hydroxypropyl cellulose, and mixtures thereof;
   (b) about 1% to about 75% by weight of a stabilizing agent selected from the group consisting of saturated polyglycolised glyceride containing $C_8$ to $C_{18}$ saturated fatty acids and shellac;
   (c) less than 10% by weight of talc; and
   (d) less than 10% by weight of magnesium stearate.

12. A controlled release pharmaceutical formulation comprising, by weight, about 39% bupropion hydrochloride, about 25% hydroxyethylcellulose, about 30% a saturated polyglycolised glyceride containing $C_8$ to $C_{18}$ saturated fatty acids, about 5% talc and about 1% magnesium stearate.

13. A controlled release pharmaceutical formulation comprising, by weight, about 39% buproprion hydrochloride, about 20% Na carboxymethyl cellulose, about 25% saturated polyglycolised glyceride containing $C_8$ to $C_{18}$ saturated fatty acids, about 10% lactose, about 5% talc, and about 1% magnesium stearate.

14. A controlled release pharmaceutical formulation comprising, by weight, about 39% bupropion hydrochloride, about 20%-hydroxyethylcellulose, about 10% lactose, about 25% saturated polyglycolised glyceride containing $C_8$ to $C_{18}$ saturated fatty acids, about 5% talc and about 1% magnesium stearate.

15. A controlled release pharmaceutical formulation comprising, by weight, about 39% bupropion hydrochloride, about 10% carboxypolymethylene, about 25% saturated polyglycolised glyceride containing $C_8$ to $C_{18}$ saturated fatty acids, about 20% lactose, about 5% talc and about 1% magnesium stearate.

16. A controlled release pharmaceutical formulation comprising, by weight about 39% bupropion hydrochloride, about 15% hydroxyethyl cellulose, about 5% carboxymethylene, about 10% lactose, about 25% saturated polyglycolised glyceride containing $C_8$ to $C_{18}$ saturated fatty acids, about 5% talc and about 1% magnesium stearate.

17. The formulation of claim 8, wherein the pharmaceutically acceptable excipient is a metallic salt of stearate.

18. The formulation of claim 17, wherein the metallic salt of stearate comprises a metal selected from the group consisting of aluminum, calcium, magnesium, sodium, and zinc.

19. The formulation of claim 1, wherein the controlled release pharmaceutical formulation comprises a crosslinked insoluble polymer present in an amount from about 5% to about 10% by weight.

20. The formulation of claim 7, wherein the saturated polyglycolised glyceride is present in an amount from about 20% to about 75% by weight.

21. The formulation of claim 20, wherein the saturated polyglycolised glyceride is present in an amount from about 20% to about 30% by weight.

22. The formulation of claim 1, comprising bupropion hydrochloride in an amount from about 1% to about 70% by weight.

23. The formulation of claim 22, comprising bupropion hydrochloride in an amount from about 1% to about 39% by weight.

24. The formulation of claim 22, comprising bupropion hydrochloride in an amount from about 39% to about 70% by weight.

25. The formulation of claim 22, comprising bupropion hydrochloride in an amount of about 39% by weight.

26. A controlled release pharmaceutical formulation comprising an effective amount of bupropion hydrochloride and:
   a) from about 1% to about 70% by weight of an uncrosslinked polymer selected from the group consisting of hydroxyethyl cellulose, sodium carboxymethyl cellulose, hydroxypropyl cellulose, hydroxypropylmethyl cellulose, and mixtures thereof; and
   b) from about 5% to about 30% by weight of a crosslinked insoluble polymer.

27. The formulation of claim 26, wherein the crosslinked, insoluble polymer is an acrylic acid polymer.

28. The formulation of claim 27, further comprising a stabilizing agent.

29. The formulation of claim 27, further comprising at least one pharmaceutically acceptable excipient.

30. The formulation of claim 28, wherein the stabilizing agent is selected from the group consisting of shellac and its constituent aliphatic polyhydroxy acids, ascorbic acid, benzoic acid and fumaric acid.

31. The formulation of claim 28, wherein the stabilizing agent comprises a saturated polyglycolised glyceride containing $C_8$ to $C_{18}$ saturated fatty acids.

32. The formulation of claim 31, wherein the saturated polyglycolised glyceride is present in an amount of about 1% to about 75% by weight.

33. The formulation of claim 29, wherein the pharmaceutically acceptable excipient is selected from the group consisting of sucrose, silicone dioxide, silicified microcrystalline cellulose, fatty acids, fatty acid salts, fatty acid esters, talc, and mixtures thereof.

34. The formulation of claim 27, wherein the acrylic acid polymer is a copolymer of acrylic acid.

35. The formulation of claim 31, further comprising a pharmaceutically acceptable film coat.

36. The formulation of claim 33, wherein the pharmaceutically acceptable excipient is a metallic salt of stearate.

37. The formulation of claim 36, wherein the metallic salt of stearate comprises a metal selected from the group consisting of aluminum, calcium, magnesium, sodium, and zinc.

38. The formulation of claim 26, wherein the controlled release pharmaceutical formulation comprises an uncrosslinked polymer present in an amount from about 10% to about 30% by weight.

39. The formulation of claim 38, wherein the controlled release pharmaceutical formulation comprises an uncrosslinked polymer present in an amount from about 20% to about 30% by weight.

40. The formulation of claim 39, wherein the controlled release pharmaceutical formulation comprises an uncrosslinked polymer present in an amount from about 20% to about 25% by weight.

41. The formulation of claim 26, wherein the controlled release pharmaceutical formulation comprises a crosslinked insoluble polymer present in an amount from about 5% to about 10% by weight.

42. The formulation of claim 32, wherein the saturated polyglycolised glyceride is present in an amount from about 20% to about 75% by weight.

43. The formulation of claim 42, wherein the saturated polyglycolised glyceride is present in an amount from about 20% to about 30% by weight.

44. The formulation of claim 43, wherein the saturated polyglycolised glyceride is present in an amount from about 25% to about 30% by weight.

45. The formulation of claim 26, comprising bupropion hydrochloride in an amount from about 1% to about 70% by, weight.

46. The formulation of claim 45, comprising bupropion hydrochloride in an amount from about 1% to about 39% by weight.

47. The formulation of claim 45, comprising bupropion hydrochloride in an amount from about 39% to about 70% by weight.

48. The formulation of claim 45, comprising bupropion hydrochloride in an amount of about 39% by weight.

49. A controlled release pharmaceutical formulation comprising an effective amount of bupropion hydrochloride and:
   a) from about 1% to about 70% by weight of an uncrosslinked polymer selected from the group consisting of hydroxyethyl cellulose, sodium carboxymethyl cellulose, hydroxypropyl cellulose, hydroxypropylmethyl cellulose, and mixtures thereof;
   b) from about 1% to about 70% by weight of a crosslinked insoluble polymer; and
   c) a stabilizing agent comprising a saturated polyglycolised glyceride present in an amount from about 25% to about 30% by weight.

50. The formulation of claim 49, wherein the crosslinked, insoluble polymer is an acrylic acid polymer.

51. The formulation of claim 50, further comprising at least one pharmaceutically acceptable excipient.

52. The formulation of claim 49, wherein the stabilizing agent comprises a saturated polyglycolised glyceride containing $C_8$ to $C_{18}$ saturated fatty acids.

53. The formulation of claim 52, wherein the pharmaceutically acceptable excipient is selected from the group consisting of sucrose, silicone dioxide, silicified microcrystalline cellulose, fatty acids, fatty acid salts, fatty acid esters, talc, and mixtures thereof.

54. The formulation of claim 50, wherein the acrylic acid polymer is a copolymer of acrylic acid.

55. The formulation of claim 53, wherein the pharmaceutically acceptable excipient is a metallic salt of stearate.

56. The formulation of claim 55, wherein the metallic salt of stearate comprises a metal selected from the group consisting of aluminum, calcium, magnesium, sodium, and zinc.

57. The formulation of claim 49, wherein the controlled release pharmaceutical formulation comprises an uncrosslinked polymer present in an amount from about 10% to about 30% by weight.

58. The formulation of claim 57, wherein the controlled release pharmaceutical formulation comprises an uncrosslinked polymer present in an amount from about 20% to about 30% by weight.

59. The formulation of claim 58, wherein the controlled release pharmaceutical formulation comprises an uncrosslinked polymer present in an amount from about 20% to about 25% by weight.

60. The formulation of claim 49, wherein the controlled release pharmaceutically formulation comprises a crosslinked insoluble polymer present in an amount from about 5% to about 30% by weight.

61. The formulation of claim 49, wherein the controlled release pharmaceutical formulation comprises a crosslinked insoluble polymer present in an amount from about 5% to about 10% by weight.

62. The formulation of claim 49, comprising bupropion hydrochloride in an amount from about 1% to about 70% by weight.

63. The formulation of claim 62, comprising bupropion hydrochloride in an amount from about 1% to about 39% by weight.

64. The formulation of claim 62, comprising bupropion hydrochloride in an amount from about 39% to about 70% by weight.

65. The formulation of claim 62, comprising bupropion hydrochloride in an amount of about 39% by weight.

* * * * *